US006284952B1

(12) United States Patent
Heo et al.

(10) Patent No.: US 6,284,952 B1
(45) Date of Patent: Sep. 4, 2001

(54) TRANSGENIC PLANTS WITH DIVERGENT [SCAM4 OR] SCAM5 GENE TO ACHIEVE MULTIPLE DISEASE RESISTANCE

(75) Inventors: Won Do Heo; Moo Je Cho, both of Kyeongnam; Pill-Soon Song; Chang Ho Chung, both of Kwangju, all of (KR)

(73) Assignee: Korea Kumho Petrochemical Co., Ltd. (KR)

( * ) Notice: Subject to any disclaimer, the term of this patent is extended or adjusted under 35 U.S.C. 154(b) by 0 days.

(21) Appl. No.: 09/239,909

(22) Filed: Jan. 29, 1999

(51) Int. Cl.[7] ............................. A01H 5/00; C12N 5/14; C12N 15/82
(52) U.S. Cl. .................................. 800/317.3; 435/320.1; 435/414; 435/419; 800/279; 800/301
(58) Field of Search ........................... 435/69.1, 320.1, 435/419, 468, 414; 800/279, 301, 317.3, 294

(56) References Cited

U.S. PATENT DOCUMENTS

| | | | |
|---|---|---|---|
| 5,530,187 | 6/1996 | Lamb et al. | 800/205 |
| 5,629,470 | 5/1997 | Lam et al. | 800/205 |

OTHER PUBLICATIONS

De Block M. "The cell biology of plant transformation: Current state, problems, prospects and the implications for the plant breeding." Euphytica 71: 1–14, 1993.*
Lee SH, et al. Gen Bank Accession No. L01433, 1993.*
Horsch et al.; Leaf Disc Transformation; Plant Molecular Biology Manual A5: 1–9 (1988).
Gynheung et al.; Binary Vectors; Plant Molecular Biology Manual A3: 1–19 (1988).
Levine et al.; $H_2O_2$ from the Oxidative Burst Orchestrates the Plant Hypersensitive Disease Resistance Response; Cell, vol. 79, Nov. 18, 1994; 583–593.
Greenberg et al.; Programmed Cell Death in Plants: A Pathogen–Triggered Response Activated Coordinately with Multiple Defense Functions; Cell, vol 77, May 20, 1994; 551–563.
Dixon et al.; Early Events in the Activation of Plant Defense Responses; Annu. Rev. Phtopathol, 32, 1994; 479–501.
Delaney et al.; A Central Role of Salicylic Acid in Plant Disease Resistance; Science, vol. 266, Nov. 18, 1994; 1247–1250.
Mittler et al.; Coordinated Activation of Programmed Cell Death and Defense Mechanisms in Transgenic Tobacco Plants Expressing a Bacterial Proton Pump; The Plant Cell, vol 7, Jan. 1995; 29–42.
Lee et al.; Identification of a Novel Divergent Calmodulin Isoform from Soybean Which Has Differential Ability to Activate Calmodulin–dependent Enzymes; The Journal of Biological Chemistry; vol 270, No. 37, Sep. 15, 1995; 21806–21812.
Beffa et al.; Cholera Toxin Elevates Pathogen Resistance and Induces Pathogenesis–Related Gene Expression in Tobacco; The EMBO Journal, vol 14, No. 23, 1995; 5753–5761.
Levine et al.; Calcium–mediated Apoptosis in a Plant Hypersensitive Disease Resistance Response; Current Biology; vol 6, No. 4; 1996; 427–437.
Jabs et al.; Initiation of Runaway Cell Death in an Arabidopsis Mutant by Extracellular Superoxide; Science, vol. 273; Sep. 27, 1996; 1853–1856.
Ryals et al.; Systemic Acquired Resistance; The Plant Cell, vol 8; Oct., 1996; 1809–1819.
Dangl et al.; Death Don't Have No Mercy: Cell Death Programs in Plant–Microbe Interactions; The Plant Cell, vol. 8; Oct., 1996; 1793–1807.
Jackson et al.; Plant–Microbe Interactions: Life and Death at the Interface; The Plant Cell, vol 8; Oct., 1996; 1651–1668.
Bergey et al; Polypeptide Signaling for Plant Defensive Genes Exhibits Analogies to Defense Signaling in Animals; Proc. Natl. Acad. Sci., vol. 93; Oct., 1996; 12053–12058.
Lee et al.; Differential Activation of NAD Kinase by Plant Calmodulin Isoforms; The Journal of Biological Chemistry; vol. 272, No. 14; Apr. 4, 1997; 9252–9259.
Durner et al.; Salicylic Acid and Disease Resistance in Plants; Elsevier Science Ltd.; vol. 2, No. 7, Jul., 1997; 266–274.

* cited by examiner

Primary Examiner—Amy J. Nelson
(74) Attorney, Agent, or Firm—Mathews, Collins, Shepherd & Gould, P.A.

(57) ABSTRACT

The present invention provides transgenic plants and plant cells thereof which have been transformed with the soybean calmodulin isoform (SCaM5) gene to exhibit greatly enhanced resistance to a wide spectrum of plant pathogens. The present invention also provides the expression vector containing SCaM5 gene and to host cells into which the gene in the expression vector has been introduced to plant pathogens-resistant plants. Transgenic plants expressing a heterologous SCaM5 gene show increased resistance to fungi, bacteria and viruses which normally infect the plants.

26 Claims, 8 Drawing Sheets

Complete nucleotide and deduced amino acid sequences of SCaM-4

```
   1    ATTTCTTACCTCTGTAGGAAAAATCAAACTCACATACTTACCGGATGAGTCTGTTT
  57    CTTACCGAGGACAAGCTTTATAAGTGTCTGAGTCAGTCTTCTGGTGCAAGCAAAGCAACC
 117    AGCTAGCGTGGTCTTTGGGTGGGTGGTGTGTGGAAATTGGATATTGATGAGAACGCAGAC
 177    TCTACACACCTCCCCATACTCCATACTCCATACCCTTTTCAAGTTTGAATTAATCCCTTC
 237    TTGTTTTGTCCCCTAAACACCAAACCCTTCCAGCTGTCAAGATTTTCTCCGTATTATACT
 297    AATCAAATTAAATATCATCATACATTAAAAAATCATTCAGCGCATTTAAACCATCGTGCC
 357    CCACCCCATTTGTACTATACTACTATGTAACAATTACAATTACAATGTGATTCTTTTTTA
 417    CACAATAAAGCCACGAGTATGGCAACAAAATGCAAGTCATATACTTAATTTGACTCGGTA
 477    AATTAAAATTTTAAAAGAAATCTTGCAAGACTAGCTAGCTAGCATCACCTAAGTTCTACA
 537    ATATAGCCCAGCTAGGATTGAGCTATACTCAACTCAACACATCATTCTCTCTTTCCCTCT
 597    CTATCTCTATCTCTCTTTCTCTGTCTCTTTTCTGGTTGAAGTTTGAAAGACAAATACACC

657    ATGGCAGATATCCTGAGTGAAGAACAGATTGTTGATTTTAAAGAGGCCTTTGGCTTGTTT
         M  A  D  I  L  S  E  E  Q  I  V  D  F  K  E  A  F  G  L  F

717    GACAAAGATGGAGATGGTTGCATTACTGTGGAAGAACTTGCCACTGTCATTCGGTCATTG
         D  K  D  G  D  G  C  I  T  V  E  E  L  A  T  V  I  R  S  L

777    GATCAGAACCCCACTGAAGAAGAGCTCCAAGATATGATAAGCGAAGTCGATGCAGATGGC
         D  Q  N  P  T  E  E  E  L  Q  D  M  I  S  E  V  D  A  D  G

837    AATGGAACCATTGAATTTGACGAGTTCTTGAGCTTGATGGCCAAGAAAGTTAAAGACACT
         N  G  T  I  E  F  D  E  F  L  S  L  M  A  K  K  V  K  D  T

897    GATGCAGAGGAGGAGCTCAAAGAAGCTTTCAAGGTTTTTGACAAAGATCAAAATGGCTAC
         D  A  E  E  E  L  K  E  A  F  K  V  F  D  K  D  Q  N  G  Y

957    ATATCAGCTAGTGAGTTGAGACACGTAATGATCAATCTAGGGGAAAAACTAACCGATGAA
         I  S  A  S  E  L  R  H  V  M  I  N  L  G  E  K  L  T  D  E

1017    GAGGTGGAGCAGATGATTAAAGAAGCAGATTTGGACGGTGATGGCCAAGTTAACTATGAG
         E  V  E  Q  M  I  K  E  A  D  L  D  G  D  G  Q  V  N  Y  E

1077    GAATTCGTCAAGATGATGATGACCGTTCGATGAAACACTCTCACCTAATTAATTGGATTG
         E  F  V  K  M  M  M  T  V  R  *

1137    GACACCAATTTGTTAATTCAAAATTCATTGGCTTCCAACCTCCCAATGAAATAAGTGTTC
1197    TTTCTTTATTATTGTTTGTTGTATTGTACTATTATTCTACTTGTACTTAGTAATGACCAA
1257    GCAGTAGATTGGCACCCCATTCCATTTGATCCATTCCAAAATTAAATTACTATTCTTGT
1317    AATTTTAGTTCAGTACATTTTCTATCCTCCGAGAGTAAGAAACCCAAGGAGCATATCTAC
1377    CCATTAATTATGCATGACTTTTACC
```

FIG.7

Complete nucleotide and deduced amino acid sequences of SCaM-5

```
1                                                        CTCCCTCT
9   CTCTTTTCTAAGTCACAAAATATTGTCTTAGTTTTCATTTGAAGCTCAAACATTAACACC
69  ATGGCAGATGTTCTGAGTGAAGAACAGATTAGTGAGATCAAAGAAGCCTTTGGCTTGTTT
     M  A  D  V  L  S  E  E  Q  I  S  E  I  K  E  A  F  G  L  F

129 GACAAAGATGGTGATGGGTGCATTACTGTGGACGAATTTGTCACGGTTATCCGGTCATTG
     D  K  D  G  D  G  C  I  T  V  D  E  F  V  T  V  I  R  S  L

189 GTTCAGAACCCCACAGAAGAAGAGCTCCAAGACATGATAAACGAGGTAGATGCAGATGGT
     V  Q  N  P  T  E  E  E  L  Q  D  M  I  N  E  V  D  A  D  G

249 AATGGAACCATTGAATTTGTTGAGTTTTTGAACTTAATGGCCAAGAAAATGAAGGAAACT
     N  G  T  I  E  F  V  E  F  L  N  L  M  A  K  K  M  K  E  T

309 GATGAAGAGGAAGATCTCAAAGAGGCTTTCAAGGTGTTTGACAAGGATCAAAATGGCTAC
     D  E  E  D  L  K  E  A  F  K  V  F  D  K  D  Q  N  G  Y

369 ATTTCAGCAAGTGAGTTGAGACACGTTATGATCAATCTGGGTGAAAAACTAACTGATGAG
     I  S  A  S  E  L  R  H  V  M  I  N  L  G  E  K  L  T  D  E

429 GAGGTGGAGCAGATGATTGAAGAAGCAGATTTGGATGGTGATGGTCAAGTTAATTATGAT
     E  V  E  Q  M  I  E  E  A  D  L  D  G  D  G  Q  V  N  Y  D

489 GAATTTGTCAAGATGATGATGACTATTGGATGAAATTTTCAAACAACAAATTTATTGTTC
     E  F  V  K  M  M  M  T  I  G  *

549 GAATTCGATCATTTGGGCCCCAATCTCATTCACTCGCATGAAATAATAAGTCTTCCAATC
609 AATTTTTGGTGTATTTTACTTGTAGCACATGATATGAATGACCAATGTATTAGAGTGACA
669 TCTCAGCCAATTTGATTTGTTCAAACTCCAACCCATAATTATTCTTTCAGTTTTAGTTTA
729 GCATTCCTTATGTTTTAAAATTAATTAGAGGGAATTTATTCAAGAACTTCTGAAATTAGA
789 CTCTTTTTTGAAAGATTAATGTATGCTACAATTTATTCTTTCTCTTGTGAACATGGTATT
849 GCTACAATTTATTTATATCATTCAGAAAAATAAAAACAGCACAAGAATTAAACAAAAA
909 AAAAAAA
```

FIG. 8

TRANSGENIC PLANTS WITH DIVERGENT [SCAM4 OR] SCAM5 GENE TO ACHIEVE MULTIPLE DISEASE RESISTANCE

The present invention relates to transgenic plants containing at least a calmodulin isoform (SCaM4 or SCaM5) gene to achieve multiple disease resistance against a wide variety of plant pathogens.

BACKGROUND OF INVENTION

The present invention refers to transgenic plants and plant cells, which have been transformed with the soybean calmodulin isoform genes (SCaM4 and SCaM5) to exhibit greatly enhanced resistance to a wide spectrum of plant pathogens. The present invention also provides the expression vector containing said genes and to host cell into which said genes in the expression vector have been introduced to plant pathogens-resistant plants. Transgenic plants expressing a heterologous SCaM4 or SCaM5 show increased resistance to fungi, bacteria and viruses which normally infect the plants.

Plants are constantly being challenged by aspiring pathogens. There are great economic losses caused by pathogenic attacks against higher plants in which the natural defenses of plants are inadequate or fail to respond and defend the plants against damage by pathogens. Therefore, control of various plant pathogens is very important in agriculture. Extensive efforts have been focused on controlling pathogenic diseases in crops. However, little success has been achieved by breeding programs to select for crops that are more resistant to pathogens. Furthermore, successful pathogen invasions and diseases ensue if the preformed plant defenses are inappropriate, the plant does not detect the pathogens, or the activated defense responses are ineffective.

It is well known that the resistance of plants to invading pathogens is accompanied by the deployment of a complex array of defense responses (Jackson et al. 1996. Plant Cell 8:1651–1668). When the pathogen carries a specific avirulence (avr) gene and the plant host contains a cognate resistance, the formation of local lesions occurs at the site of infection that results in inhibition of pathogen growth (termed the hypersensitive response; HR) (The Hypersensitive Reaction in Plants to Pathogens: A Resistance Phenomenon. Goodman, R. N. and Novacky, A. J., APS Press, St. Paul. 1994). Therefore, a plant expressing a particular resistance (R) gene is specifically resistant to pathogens expressing the corresponding avr gene. In addition to the hypersensitive response, a secondary defense response can be triggered that renders uninfected parts of the plant resistant to a variety of virulent pathogens (termed systemic acquired resistance; SAR). The interactions between plants and pathogens lead to a series of defense signal transduction events, including oxidative burst, transient $Ca^{+2}$ increase, salicylic acid accumulation, the synthesis of high levels of pathogenesis-related proteins, phytoalexin biosynthesis and defense gene activations. Accumulating evidence implicates the involvement of a $Ca^{2+}$ signal in certain plant defense responses. A $Ca^{2+}$ ion influx is one of the earliest events in challenged cells (Dixon et al. 1994. Annu. Rev. Phytopathol. 32:479–501) and has been shown to be essential for the activation of defense responses such as phytoalexin biosynthesis, induction of defense-related genes, and hypersensitive cell death (Levine et al. 1996. Curr. Biol. 6:427–437). However, direct evidences for the involvement of CaM in plant disease resistance responses have been unavailable.

Various approaches have been utilized for attempting to control deleterious fungi, bacteria, viruses and even nematodes. One approach is the application of certain naturally occurring bacteria which inhibit or interfere with fungi or nematodes. Another approach is breeding for resistance, which is primarily focused on the manipulation of minor resistance genes which make small quantitative contributions to the overall resistance of the plant. However, there is often an inability of the plants to recognize the pathogen to cause the. defenses of the plants to be induced. Furthermore, the protection provided by these approaches is much narrower than that rendered by full-fledged systemic acquired resistance, and the degree of resistance is much less significant.

Transgenic plants of this invention contain similar levels of specific divergent SCaM4 or SCaM5 protein (0.3–0.5 μg/mg total soluble leaf protein) to that of the highly conserved CaM isoforms (SCaM1, SCaM2, and SCaM3) in wild type plants. Upon challenge with pathogens, it has been found that the transgenic plants provided by this invention show long-lasting, broad-spectrum resistance against a variety of pathogens (fungal, viral and bacterial pathogens), similar to systemic acquired resistance. To our knowledge, this is the first in vivo evidence not only for the functional differences among CaM isoforms but also for a central role of SCaM4 and SCaM5 for a broad spectrum of pathogen (including virus, bacteria and fungi) resistance in plants.

SUMMARY OF INVENTION

Provided by this invention are higher plant cells transformed with the SCaM4 or SCaM5 gene, resulting in enhanced multiple-resistance to pathogenic attack by one or more plant pathogens. Provided also are the expression vectors accessing SCaM4 or SCaM5 gene which can be able to transform the cells of higher plants according to the present invention.

Figure 1:
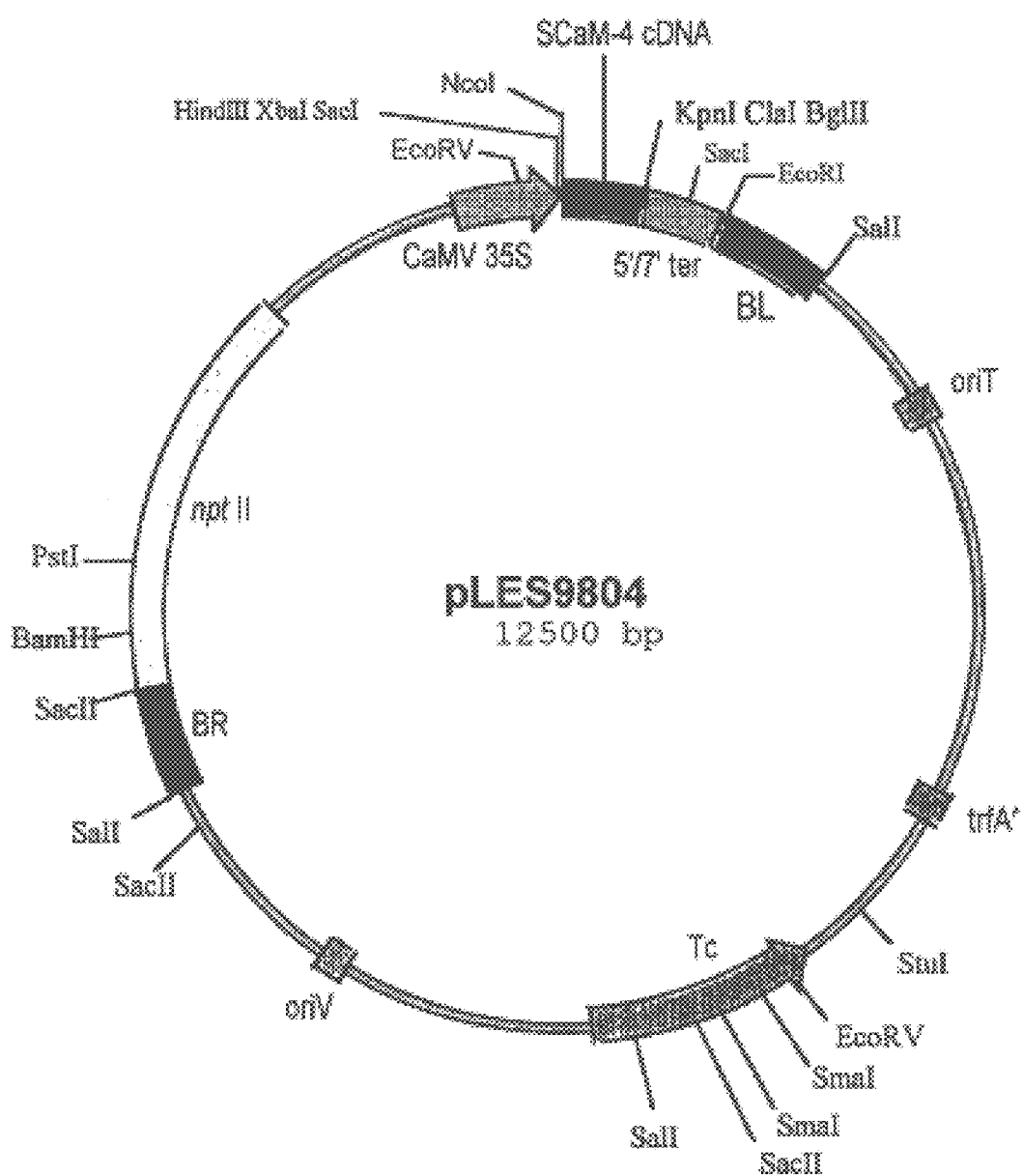
FIG. 1. Schematic diagram of the plant expression vector of pLES9804 harboring an exogenous transgene encoding SCaM4 protein.
Figure 2:
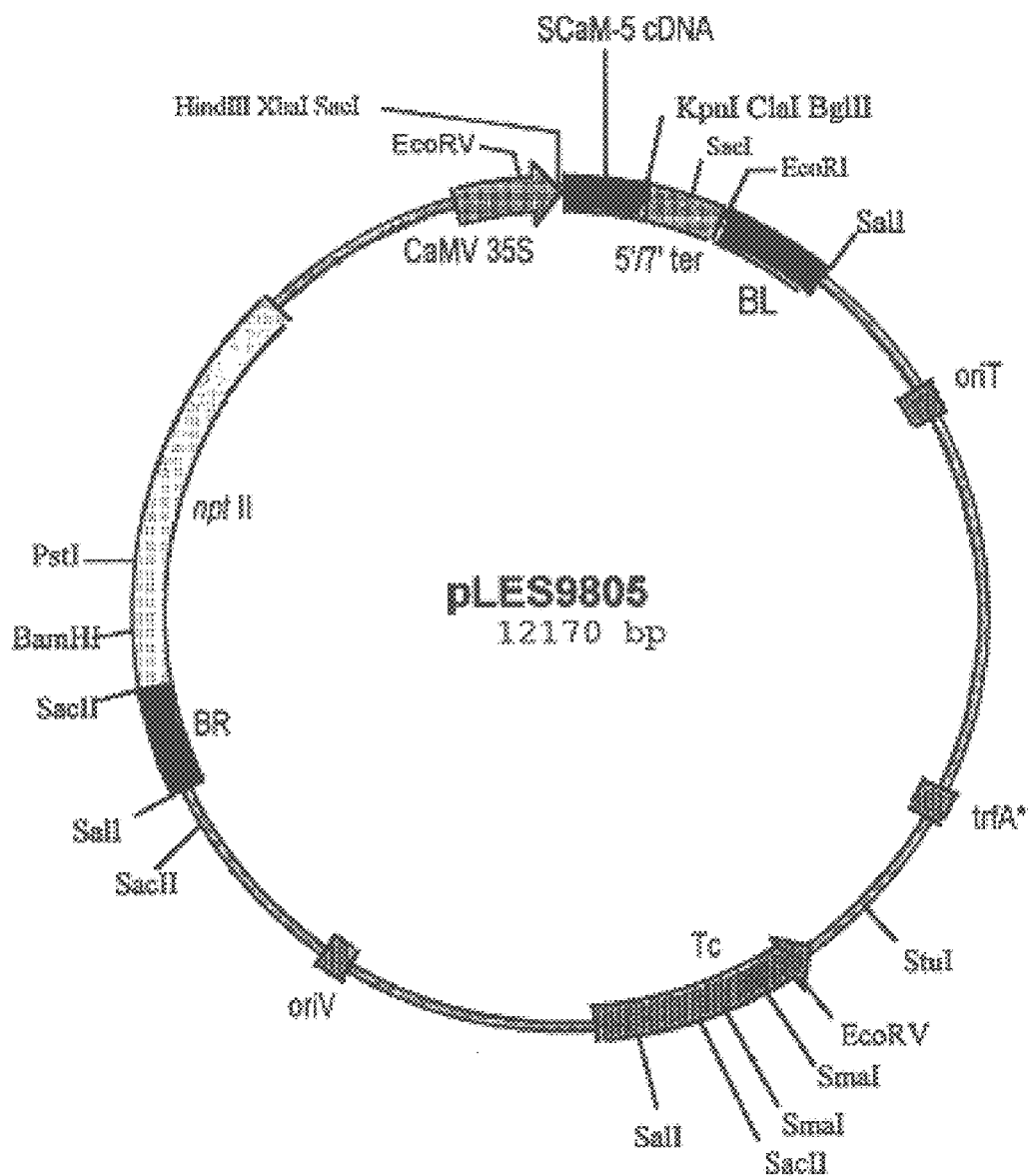
FIG. 2. Schematic diagram of the plant expression vector of pLES9805 harboring an exogenous transgene encoding SCaM5 protein.

*sitica* var. *nicotianae,* (FE+CHX) fungal elicitor plus 1 µg/ml cycloheximide, (FE+BAPTA) fungal elicitor plus 5 mM 1,2-bis-(o-aminophenoxy)-ethane-N,N,N-',N'-tetraacetic acid, ($Ca^{2+}$+A23187) 25 µM $Ca^{2+}$ ionophore A23187 plus 5 mM $CaCl_2$, ($H_2O_2$) 2 mM hydrogen peroxide, (G-GO) glucose and glucose oxidase system, (X-XO) xanthine and xanthine oxidase system, (SA) 2 mM salicylic acid, (JA) 100 µM jasmonic acid, (ABA) 100 µM abscisic acid.

FIGS. 4A–4D. Phenotypes of transgenic tobacco plants constitutively expressing SCaM4 or SCaM5. (A) Developmentally regulated formation of spontaneous disease lesion-like necrotic regions in the transgenic plants. The whole plant morphology of an 8-week-old representative transgenic SCaM4 plant (Right) which shows that lesions appeared only in the older leaves near bottom of the plant. A normal wild-type plant of similar age is shown on the Left. (B) A closer look at the spot-like spontaneous lesions formed on the leaf of a 10-week-old SCaM5 transgenic plant (Right). A normal leaf of a similar age is shown on the Left for comparison. (C and D) Accumulation of UV-excitable fluorescent material in the cell walls of spontaneously formed lesions. Microscopic examination of a spontaneous lesion under differential interference contrast (C) and epifluorecence (D) optics after nuclear staining of leaf tissues with 4', 6-diamidino-2-phenylindole.

FIGS. 5A–5D. Constitutive expression of PR protein genes in transgenic SCaM4 and SCaM5 tobacco plants. (A) Immunoblots showing elevated SCaM4 and SCaM5 protein levels in transgenic plants. Total soluble protein (50 µg) from three independent transgenic plant lines was analyzed for SCaM protein levels using either the anti-SCaM4 or anti-SCaM1 antibody. (B) Constitutive expression of PR protein genes in the transgenic plants. Total RNA was isolated from a wild type (WT), a control transgenic plant harboring an empty vector (CT), and three representative independent transgenic plants expressing SCaM4 (S4TG) or SCaM5 (S5TG) and examined for the mRNA levels of tobacco SAR genes (31). # indicates numbers of transgenic plant lines. (C) Expression of PR protein genes in transgenic SCaM4 and SCaM5 plants in the absence of lesions. RNA blot analysis of PR1 gene expression in healthy lesion-negative or lesion-positive leaves of the transgenic plants (indicated above lanes as – or +, respectively). (D) SA-independent PR protein gene expression. The effect of constitutive expressing SCaM4 or SCaM5 in wild-type plants or nahG transgenic plants (33) on PR protein gene expression was examined by RNA gel blot analysis using PR1a and PR5 probes. Data shown are representative results obtained from at least 10 respective independent transgenic plant lines.

FIGS. 6A–6E. Enhanced disease resistance of transgenic tobacco plants constitutively expressing SCaM4 or SCaM5. (A) Disease responses to the virulent fungal pathogen, *Phytophthora parasitica* var. *nicotianae*. At 7 days after inoculation, plants were examined for disease symptoms. Representative results of wild-type (WT) and transgenic plants expressing SCaM4 (S4TG) or SCaM5 (S5TG) are shown. (B and C) Fluorescence micrographs of leaves infected with the virulent *P. parasitica* var. *nicotianae*. Infected leaves were cleared, stained with aniline blue, and examined under an ultraviolet-light epifluorescence microscope. In leaves of the wild-type plants (B) the spreading of fungal hyphae is evident, but leaves of the transgenic plants (C) show the accumulation of UV-excitable fluorescent material in the cells surrounding the fungal penetration sites without appreciable growth of fungal hyphae. Scale bars represent 100 µm. (D) In planta bacterial growth. *Pseudomonas syringae* pv. *tabacci* was inoculated into leaves of mature wild-type (WT) and transgenic SCaM-4 (S4TG) and SCaM5 (S5 TG) plants at $10^5$ cfu/ml, and in planta bacterial growth was monitored over 5 days. Data points represent means of two determinations from five independent lines. (E) Elevated resistance of SCaM4 and SCaM5 transgenic plants to the avirulent pathogen, TMV. The second or third fully expanded young leaves from the uppermost part of plants were inoculated with TMV by gently rubbing leaves with carborundum and 2 µg/leaf TMV, and the development of HR lesions were monitored over five days. Data shown are the numbers of HR lesions formed in these plants. In all of these pathogen tests, control transgenic plants transformed with an empty vector showed results essentially similar to those of wild-type plants (data not shown).

FIG. 7. The complete nucleotide (SEQ ID NO:1) and deduced amino acid (SEQ ID NO:2) sequences of ScaM-4.

FIG. 8. The complete nucleotide (SEQ ID NO:3) and deduced amino acid (SEQ ID NO:4) sequences of ScaM-5.

DETAILED DESCRIPTION OF THE INVENTION

The present invention refers to transgenic plants and plant cells, which have been transformed with the soybean calmodulin isoform 4 or 5 (SCaM4 or SCaM5) gene to exhibit greatly enhanced resistance to a wide spectrum of plant pathogens. The present invention also provides the expression vector containing said genes and the host cell into which said genes in the expression vector have been introduced to plant pathogen-resistant plants. Transgenic plants expressing a heterologous SCaM show increased resistance to fungi, bacteria and viruses which normally infect the plants.

In an illustrative preferred embodiment of the invention, cells of tobacco plants are transformed with the divergent SCaM4 or SCaM5 gene. The transformed tobacco plants show enhanced multiple disease resistance against a variety of pathogenic attacks (fungi, viruses and bacteria). The increased multiple disease resistance will allow a higher crop yield and a reduction in the amount of fungicides applied to control decay, allowing for the marketing of more competitive agricultural products.

SCaM4 and SCaM5 genes are novel divergent calmodulin isoform from soybean which has differential ability to activate calmodulin-dependent enzymes (Lee et al. 1995. J. Biol. Chem. 270:21806–21812). SCaM5 exhibits ~78% identity of nucleotide sequence with SCaM4.

A transgenic plant according to the present invention refers to a plant or plant material that contains one or more inheritable recombinant nucleic acid expression cassettes encoding at least SCaM4 or SCaM5. Preferably the invention transgenic tobacco plant contains at least either SCaM4 or SCaM5 or both.

As used herein, an "overexpressed" SCaM refers to a protein that is produced in higher amount than are produced endogenously. Overexpression can be achieved, for example, by linking a transgene to an appropriate constitutive promoter, such that the transgene is continually expressed. Alternatively, the transgene can be linked to a strong, inducible promoter so that overexpresion can occur on demand. Suitable levels of the overexpression include the expression of trasngene at least about 10-fold over the naturally occurring level of expression of the endogenous transgene being especially preferred. Constitutive promoters suitable for use in the practice of the present invention are widely available and are well known in the art, including the cauliflower mosaic virus 35S (CaMV35S) promoter (U.S. Pat. No. 5,097,925) and the like.

The SCaM4 and SCaM5 described in the present invention are encoded by recombinant transgene molecules. As used herein, the term "transgene" refers to a DNA or RNA molecule. Transgenes employed herein encode a biologically active amino acid sequence (i.e., protein).

Transgenes encoding the SCaM4 or SCaM5 protein are typically contained in the expression cassette. The expression cassette refers to a DNA molecule that is able to direct the transcription and translation of a structural gene (i.e., cDNA) so that a desired protein is synthesized. The expression cassette comprises at least one promoter operatively linked to at least one transgene encoding a desired protein, and a transcription terminator sequence. Thus, the protein-encoding segment is transcribed under regulation of the promoter region, into a transcript capable of providing, upon translation, the desired protein. Appropriate reading frame positioning and orientation of the various segments of the expression cassette are within the knowledge of persons of ordinary skill in the art.

As used herein the term "plasmid" or "vector" refers to circular, double-stranded DNA loops, which are not bound to the chromosome. A plasmid contains DNA capable of causing the expression of DNA sequences contained therein, where such sequences are in operational association with other sequences capable of effecting their expression, such as promoter sequences. Presently preferred vectors for producing invention transgenic tobacco plants are the plasmids pLES9804 and pLES9805, described hereinafter in the EXAMPLES section.

The term "multiple disease resistance", when used in the context of comparing the level of resistance between an invention transgenic plant and another plant, refers to the ability of the invention transgenic plant to maintain a desirable phenotype in the face of attack, relative to a non-transgenic plant or a single-gene transgenic plant. The level of resistance can be determined by comparing the physical characteristics of the invention plant to non-transgenic plants that either have or have not been exposed to pathogenic infection.

Methods of introducing the constructs employed herein into suitable host cells, as well as methods applicable for culturing said cells containing a gene encoding a heterologous protein, are generally known in the art. According to the invention, the vector is introduced into the host cell by *Agrobacterium tumefaciens* EHA101. In addition to plant transformation vectors derived from Agrobacterium, high velocity ballistic penetration can be used to insert the DNA constructs of this invention into plant cells. Yet another method of introduction is the fusion of protoplasts with other entities. The DNA may also be introduced into the plant cells by the electroporation.

In one embodiment of the present invention, two expression cassettes containing transgenes encoding SCaM4 or SCaM5, respectively, are prepared as described in the EXAMPLE. The expression cassettes are combined into a single expression vector, to form a DNA construct, which comprises two individual genes encoding SCaM4 or SCaM5. The vector is then inserted into *A. tumefaciens* cells which contain a disarmed Ti plasmid.

After transformation, transformed plant cells or plants comprising the said DNA constructs can be identified by employing a selectable marker. Transformed plant cells can be selected by growing the cells in growth medium containing an appropriate antibiotics.

After selecting the transformed cells, one can confirm expression of the desired heterologous gene. Simple detection of mRNA encoded by the inserted DNA can be achieved by Northern blot hybridization. The inserted sequence can be identified by Southern blot hybridization, as well. Once the presence of the desired transgenes is confirmed, whole plant regeneration can be achieved. All plants which can be regenerated from cultured cells or tissues can be transformed by the present invention.

Two separate transgenic plants that contain expression cassettes having at least one transgene can be sexually crossed using cross-pollination method to produce a transgenic plant of the present invention. Any of a number of standard breeding techniques can be used, depending upon the species to be crossed.

Plants contemplated for use in the practice of the present invention include both monocotyledons and dicotyledons. Exemplary monocotyledons contemplated for use in the practice of the present invention include rice, wheat, maize, barley as well as other grains. Exemplary dicotyledons include tobacco, tomato, potato, soybean, and the like.

The invention will then be described in greater detail by reference to the following non-limiting examples.

RESULTS

SCaM-4 is 1,429 bp long and has 664 bp of 5' untranslated region, 450 bp of protein coding sequences, and 315 bp of 3' untranslated region. Protein coding region is composed of 149 amino acids. The polyadenylation signal, ATTAAA was shown in 3' untranslated region.

Nucleotide sequence comparison to other plants CaMs, SCaM-1, 2, 3 and bovine CaM reveals more than 70% sequence homology within their protein coding regions. However, the 5' and 3' untranslated regions of SCaM-4 showed no significant homology to other SCaMs, indicating that this cDNA clone is derived from different gene transcripts in soybean genome. In case of actin gene, nucleotide sequence divergency is only 11 to 15% between plant and non-plant actin, and 6 to 9% within soybean actin gene family members. SCaM4 has 30% divergency compared to SCaM-1, 2, 3 that is surprisingly high.

Deduced amino acid sequence comparison of SCaM-4 with higher plants CaM and bovine CaM revealed that SCaM-4 shares more than 80% sequence identity. Otherwise, plant CaMs share more than 95% sequence identity with each other. Interestingly, the deduced amino acid sequences of SCaM-4 is highly diverged. SCaM-4 is exchanged with SCaM-1,2,3 by 32 amino acids, potato CaM by 26 amino acids, and bovine CaM by 28 amino acids.

The noticeable exchange is Phe to Tyr in the 3rd $Ca^{2+}$-binding domain. In bovine CaM, the Tyr residue thought be phosphorylation that functions allowing it to react with target proteins in the absence of $Ca^{2+}$. The second noticeable exchange is positive charged Lys to negative charged Glu in the 1st $Ca^{2+}$-binding domain, and Pro to Asp in the 2nd $Ca^{2+}$-binding domain. The exchange of $Ca^{2+}$-binding domain inferred that $Ca^{2-}$-binding affinity and conformational changes are affected. Further noticeable exchange is $Gly^{41}$ to Asp and $Ser^{81}$ to Ala. This residue is essential to helix bending sites, to allow clasping of the two lobes on to the large variety of basic amphiphilic α-helices in the various targets. $Gly^{41}$ is highly conserved through the evolution presumably because its small size makes the sharp bend possible. The bulkier and charged Asp should interfere with this bend. In addition, the replace Val-145 with Met that three Met, short and unbranched, in the hydrophobic patches may provide the individual contact for the activation of specific targets.

SCaM-5 consists of 68 bp of 5' untranslated region, 450 bp of open reading frame, and 397 bp of 3' untranslated region. Protein coding region is composed of 149 amino acids. The polyadenylation signal was not found.

Nucleotide sequence of other plants CaMs, SCaM-1, -2, -3, -4 and bovine CaM reveals more than 70% sequence homology within their protein coding regions. However, the 5' and 3' untranslated regions of SCaM-5 showed no significant homology to other SCaMs, indicating that this cDNA clone is derived from different gene transcripts in soybean genome. SCaM-5 has an interesting sequence motif of ATTTA in the 3' untranslated region. This motif was known as MRNA destabilizing motif in eukaryote which was recognized by RNase or other cellular factors.

Deduced amino acid sequence comparison of SCAM-5 with higher plant CaMs and bovine CaM revealed that SCaM-5 share more than 80% sequence identity with SCaM4. Interestingly, the deduced amino acid sequences of SCaM-5 are highly diverged from other SCaMs and plant CaMs. SCaM-5 has 18 amino acid substitutions to SCaM4 and is the most divergent SCaM isoform. These exchanges include five Asp to Glu exchanges as found in the case of SCAM-1 and -2. One of the noticeable exchanges of amino acid residues in SCaM4 and -5 is the $Tyr^{99}$ residue found in the 3rd $Ca^{2+}$-binding domain. The $Tyr^{99}$ residue at the 3rd $Ca^{2+}$-binding domain is found only in animal CaM and not yet found in plant CaM sequences. The $Tyr^{99}$ residue has been thought to be a candidate for phophorylation target by src kinase and insulin receptor kinase. Furthermore the $Ser^{81}$ residue which is conserved in all identified CaM sequences is substituted to Ala or Glu in SCaM-4 and -5, respectively. The $Ser^{81}$ residue is observed to be phosphorylated by casein kinase II in vitro. As clearly indicated from the sequence comparisons, SCaM-5 can be classified into a new type CaM group together with SCaM-4.

Figure 3:
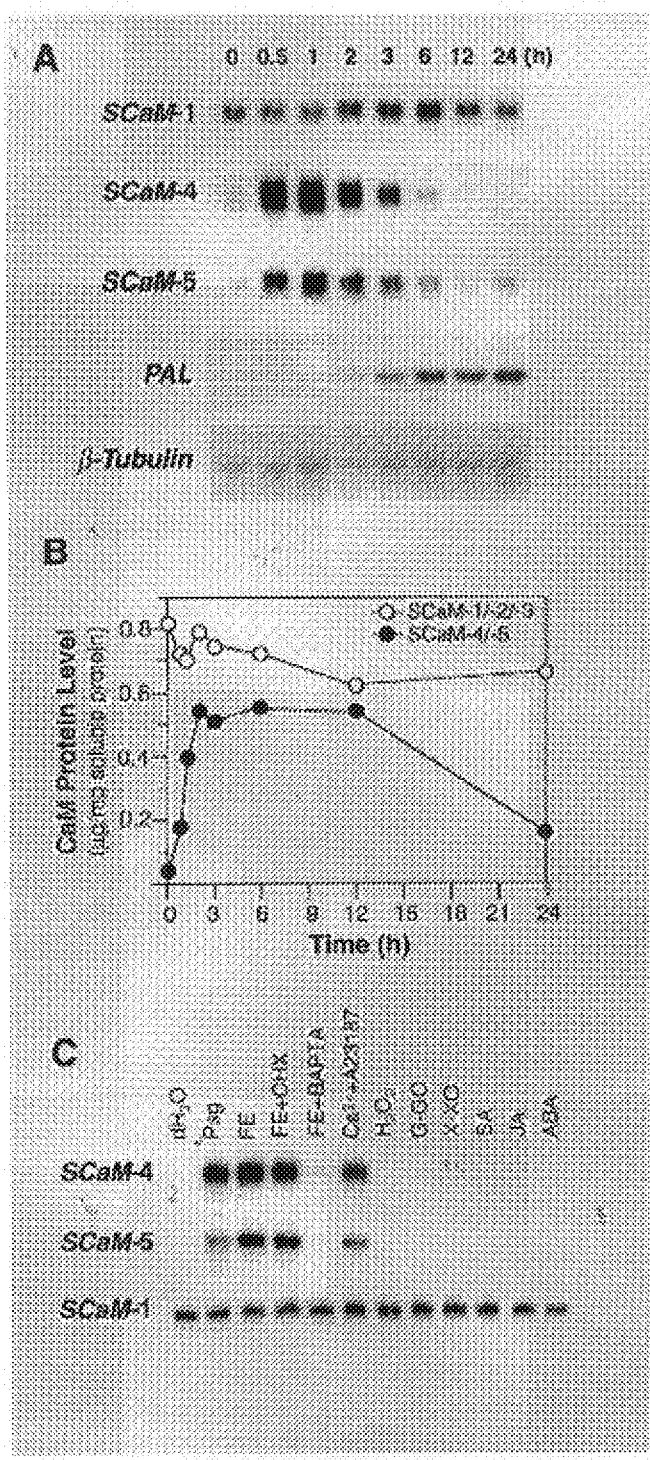
FIGS. 3A–3A Rapid induction of SCaM4 and SCaM5 during plant defense response. (A) Effect of a fungal elicitor on the expression of soybean calmodulin (SCaM) genes. Soybean cell suspension culture (SB-P) was treated with fungal elicitor prepared from *Fusarium solani*, total RNA was isolated at the indicated times, and analyzed for SCaM1, SCaM4, SCaM5, phenylalanine ammonia-lyase (PAL), and β-tubulin mRNA. (B) Changes in SCaM protein levels upon fungal elicitor treatment. SB-P cells were treated as described in (A) and relative protein levels of SCaM4/5 or SCaM1/2/3 were examined by immunoblot analysis using either anti-SCaM4 or anti-SCaM1 antibody, respectively (16). Relative protein levels of SCaM isoforms were calculated by comparing band intensities and areas in autoradiograms with those of known quantities of standard SCaM1 or SCaM4 proteins using scanning densitometry. (C) Effect of various defense signaling molecules on the expression of SCaM genes. SB-P cells were treated for 1 h as indicated above the lanes and the mRNA levels of the SCaM genes were examined by Northern blot analysis. ($dH_2O$) water control, (Psg) *Pseudomonas syringae* pv. *glycinea* carrying avrC, (FE) fungal elicitor prepared from *Phytophthora para-*

Treatment of soybean cell suspension cultures with a non-specific fungal elicitor prepared from *Fusarium solani* resulted in a dramatic rise (>10 fold) in MRNA encoded by SCaM4 and SCaM5 (FIG. 3A), the two SCaM genes whose sequences are most divergent from other CaM genes and subsequently will be referred to as the divergent CaM. Their MRNA levels peaked at 1 h and then slowly declined to basal levels by 12 h. The basal expression levels of these two SCAM genes in untreated cells were low in comparison to those of the highly conserved SCaM genes, SCAM1, 2, and 3. In contrast to SCaM4 and SCaM5, expression of these three conserved SCAM genes was not activated by the elicitor treatment (FIG. 3A). Consistent with the changes in SCaM MRNA levels, the protein levels of SCaM4/5 but not SCaM1/2/3 also increased within 30 min of the treatment (FIG. 3B). SCaM4/5 protein levels reached their maximum of approximately 0.5 μg per mg of soluble proteins after 2 h and then slowly declined after 12 h. In contrast, SCaM1/2/3 protein levels were not changed significantly by the fungal elicitor treatment. Interestingly, the induction of the SCaM4 and SCaM5 genes expression preceded that of the phenylalanine ammonia-lyase gene whose mRNA level began to increase 3 h after treatment (see FIG. 3A). An elicitor prepared from *Phytophthora parasitica* var. *nicotianae* had a similar effect on the expression of these CaM genes (see FIG. 3C).

We next examined the effect of several potential inducers of plant defense-related genes to gain further insight into the molecular signals involved in the induction of SCaM4 and SCaM5 gene expression. Both *P. parasitica* elicitor and a bacterial pathogen, *Pseudomonas syringae* pv. *glycinea* (Psg) carrying avrC, effectively induced SCaM4 and SCaM5 gene expression (FIG. 3C). Cycloheximide, a protein synthesis inhibitor, did not block SCaM4 and SCaM5 induction by the *P. parasitica* elicitor. In contrast, addition of a $Ca^{2+}$-chelator, 1,2-bis-(o-aminophenoxy)-ethane-N,N,N', N'-tetraacetic acid (BAPTA), abolished this induction of SCaM4 and SCaM5, whereas the $Ca^{2+}$-ionophore, A23187, alone was sufficient to induce SCaM4 and SCaM5 expression as effectively as the fungal elicitor. However, application of exogenous salicylic acid (SA; 1 mM to 5 mM) or hydrogen peroxide ($H_2O_2$; 1 mM to 10 mM) did not induce the expression of SCaM4 and SCaM5 genes during a 24 h time course (data not shown). A $H_2O_2$-generating system [glucose and glucose oxidase (Levine, A. et al. 1994. Cell 79:583–593)] and a superoxide-generating system [xanthine and xanthine oxidase (Jabs, T. et al. 1996. Science 273:1853–1856)] also failed to induce SCaM4 and SCaM5 gene expression. Two unrelated signal molecules, jasmonic acid (JA) (Bergey, D. R. et al. 1996. Proc. Natl. Acad. Sci. USA 93:12053–12508) and abscisic acid (ABA) (Giraudat, J. et al. 1994. Plant Mol. Biol. 26:1557–1578), also were unable to induce SCaM4 and SCaM5. These results indicate that transcriptional activation of SCaM4 and SCaM5 genes upon elicitation is a very rapid process which does not require protein synthesis and either precedes synthesis and accumulation of reactive oxygen species (ROS) and SA or is in another disease resistance signaling pathway. Furthermore, their activation was specific; signaling compounds associated with other stress responses such as wounding (JA) and drought (ABA) did not induce SCaM4 and SCaM5. However, their induction appears to be mediated by an increase of intracellular $Ca^{2+}$ concentration.

Figure 4:
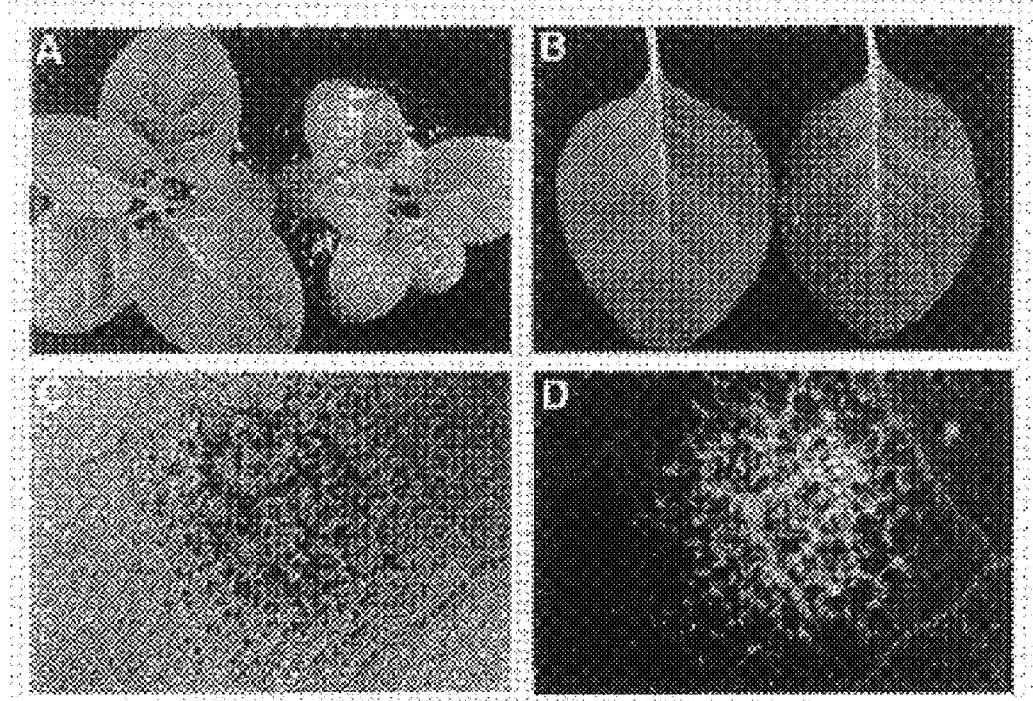

In order to examine the biological functions of these transiently induced, divergent SCAM isoforms in plant defense responses, we constructed transgenic tobacco plants that constitutively expressed SCaM4 or SCaM5 under the control of the constitutive cauliflower mosaic virus 35S promoter. Transgenic plant lines expressing SCaM4 or SCaM5 were first selected by northern analysis and verified by immunoblot analysis (Lee, S. H. et al. 1995. J. Biol. Chem. 270:21806–21812). Interestingly, the transgenic SCaM4 and SCaM5 plants often spontaneously formed disease-like necrotic spots on their leaves (FIGS. 4A and 4B). The lesions appeared first in the oldest mature leaves, while the top three to four young leaves never developed lesions. These results suggest that spontaneous lesion formation in the transgenic plants was developmentally regulated. Untransformed wild-type and empty vector-transformed control transgenic plants grown under identical conditions did not show these symptoms. To determine whether these lesions were HR-like lesions, they were examined with a fluorescence microscope. HR-like lesions accumulate fluorescent material in the cell walls that is readily visible under ultraviolet (UV) illumination (Greenberg, J. T. et al. 1994. Cell 77:551–564), while necrotic regions generated by mechanical wounding or freezing and thawing have no such fluorescence (Mittler, R. et al. 1995. Plant Cell 7:29–42). Leaves of the transgenic plants exhibited accumulation of bright UV-excitable fluorescent material in their lesions, suggesting that these necrotic lesions resemble HR-like lesions (FIGS. 4C and 4D).

Figure 5:
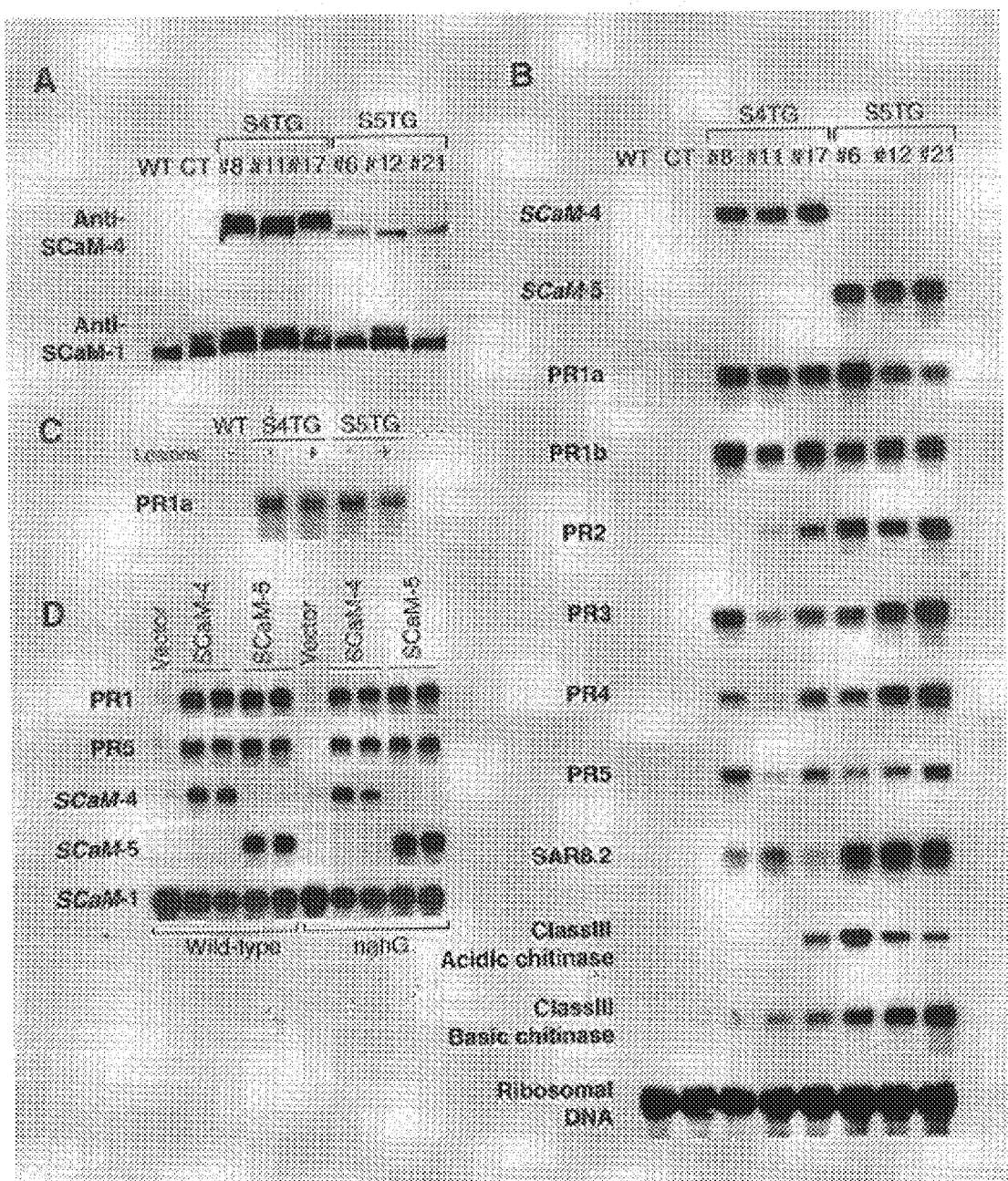

The constitutive expression of these divergent CaM isoforms SCaM4 and SCaM5 did not affect the level of the highly conserved endogenous tobacco CaM recognized by the anti-SCaM1 antibody (FIG. 5A). The anti-SCaM1 antibody recognized equally the highly conserved CaM isoforms SCaM1, SCaM2, and SCaM3 protein but not the divergent SCaM4 and SCaM5. The anti-SCaM4 antibody cross-reacted with SCaM5 but not with the highly conserved CaM isoforms (16, data not shown). The amounts of SCaM4 and SCaM5 protein in these transgenic plants were estimated to be 0.3–0.5 μg per mg total soluble leaf protein, which is similar to the maximal level of the SCaM4/5 protein induced by a fungal elicitor in soybean cells (see FIG. 3B). Furthermore, the levels of SCaM4 and SCaM5 in transgenic plants did not exceed the protein levels of the highly conserved CaM isoforms (SCaM1, SCaM2, and SCaM3). Thus, it is likely that the phenotypes of these transgenic plants is not due to high level overexpression of SCaM4 or SCaM5, which could lead to abnormal cellular responses (Durner, J. et al. 1997. Trends Plant Sci. 2:266–274), but rather is due to levels of these divergent CaM isoforms which is similar to those after activation of these genes by pathogen attack.

Spontaneous lesion forming mutants often show elevated expression of genes encoding pathogenesis-related (PR) proteins and increased resistance to pathogens (Durner, J. et al. 1997. Trends Plant Sci. 2:266–274). Interestingly, in the absence of pathogens, the transgenic SCaM4 and SCaM5 plants expressed at high levels all of the nine SAR marker genes in tobacco that are normally activated during the development of SAR (Ryals, J. A. et al. 1996. Plant Cell 8:1809–1819) (FIG. 5B). Wild-type plants and control empty vector transgenic plants grown under identical conditions did not express these genes. These SAR-associated genes were constitutively expressed throughout the growth and development of the SCaM4 and SCaM5 transgenic plants and were apparent even in the leaves of axenically grown young seedlings which had not developed lesions (FIG. 5C). Thus, expression of PR genes in the transgenic SCaM4 and SCaM5 plants was independent of lesion formation, suggesting that PR gene expression in the transgenic plants is not a consequence of cell death.

SA is known to be a natural signaling molecule for the activation of certain plant defense responses (Durner, J. et al. 1997. Trends Plant Sci. 2:266–274). The application of exogenous SA to tobacco leaves mimics the pathogen-induced SAR responses such as PR protein synthesis. In addition, endogenous SA levels in several lesion-mimic mutants are substantially higher than those of wild-type plants in the absence of pathogen challenge (Ryals, J. A. et al. 1996. Plant Cell 8:1809–1819). Furthermore, transgenic plants that constitutively expressed the bacterial nahG gene, which encodes a SA-degrading enzyme, are defective in their ability to induce SAR (Delaney, T. P. et al. 1994. Science 266:1247–1250). We, therefore, examined whether the disease resistance responses in the SCaM4 or SCaM5 transgenic plants might be due to elevation of endogenous SA levels. Surprisingly, SA levels in SCaM4 and SCaM5 transgenic plants were similar to those of wild-type plants (Table 1). Moreover, infection with tobacco mosaic virus (TMV) resulted in similar increase in SA levels in the transgenic plants and wild-type plants, demonstrating that the expression of SCaM4 and SCaM5 in the transgenic plants did not affect endogenous SA accumulation. Consistent with these observations, the presence and expression of nahg gene did not suppress the constitutive expression of PR genes in the SCaM4 and SCaM5 transgenic plants (FIG. 5D). These results strongly argue that SA is not involved in the plant disease resistance responses mediated by SCaM4 or SCaM5.

Finally, we assessed whether transgenic SCaM4 and SCaM5 plants had altered resistance to pathogen s. We used an oomycete fungal pathogen, *Phytophthora parasitica* var. *nicotianae* (the causal agent of black shank disease) to inoculate the transgenic and wild-type plants. At 5 days after *P. parasitica* inoculation, disease symptoms started to appear on the wild-type plants but not on the transgenic plants. By 7 days after inoculation, the wild-type plants had severe disease symptoms such as leaf wilting and stem rot and eventually died by 8 days after inoculation. However, the transgenic plants remained healthy without appreciable disease symptoms (FIG. 6A). The leaves of the fungus-infected wild-type plants showed uninterrupted spreading of fungal hyphae with little callous deposition (FIG. 6B). In contrast, leaves of the inoculated transgenic plants had no such growth of fungal hyphae but instead exhibited bright fluorescence related to callous deposition and accumulation of autofluorescent material in the cells surrounding the fungal penetration sites (FIG. 6C). This is characteristic of an HR. Interestingly, *P. parasitica* var. *nicotianae* is a virulent pathogen on the parental non-transformed Xanthi-nc tobacco cultivar and does not normally trigger an HR. The transgenic plants also showed enhanced resistance to a virulent bacterial pathogen, *Pseudomonas syringae* pv. *tabacci* (Pst). They successfully blocked development of disease symptoms, and the in planta growth of Pst was retarded greater than 10-fold compared to their growth in wild-type plants (FIG. 6D). In addition, transgenic SCaM4 and SCaM5 plants exhibited increased resistance to a virulent viral pathogen, TMV. The transgenic plants developed TMV-induced HR lesions approximately 12 h earlier than wild-type plants. Furthermore, the transgenic plants had fewer ~5-fold) and smaller TMV-induced lesions (FIG. 6E), which are two characteristics associated with enhanced resistance to TMV.

In this invention we have demonstrated a central role for the major $Ca^{2+}$ signal transducer, CaM, in plant defense signaling. Our results argue that the divergent CaM isoforms act as both signal receptor and transmitter of the pathogen-induced $Ca^{2+}$ signal. Divergent CaM isoforms resemble immediate early genes such as fos and jun in animal system in that certain external stimuli immediately activate their expression which then leads to cellular responses (Morgan, J. I. and Curran, T. 1989. Trends Neurosci. 12:459–462). Thus, the divergent CaM isoforms represent novel inducible components of plant defense responses.

Transgenic plants that constitutively expressed these divergent CaM isoforms had phenotypes similar to those of spontaneous lesion-mimic mutants; however, there are several notable differences. The first concerns the causal relationship between cell death and PR gene expression. While PR gene expression is tightly linked to cell death in lsd and acd mutants, it is independent of cell death in the SCaM4 and SCaM5 transgenic plants. The second major difference is SA dependence. SA levels in most lesion-nilmic mutants are substantially higher than those in normal plants (Dangl, J. L. et al. 1996. Plant Cell 8:1793–1807). In contrast, in the SCaM4 and SCaM5 transgenic plants disease resistance responses were activated without concurrent elevation of endogenous SA level. Furthermore, removal of SA in these transgenic plants by co-expression of the nahG gene did not block the constitutive expression of PR genes. These observations strongly suggest that the divergent CaM isoforms activate plant disease resistance responses via a SA-independent pathway(s).

The present invention provides the first in vivo evidence for functional differences among plant CaM isoforms. Only divergent CaM isoforms are induced by pathogens and could trigger defense responses in transgenic plants, whereas the other, highly conserved CaM isoforms such as SCaM1 and SCaM2 did not have these properties (data not shown). The $Ca^{2+}$/CaM pathway in ROS production is thought to be mediated by the highly conserved CaM isoforms since the divergent CaM isoforms are unable to activate NAD kinase (Lee, S. H. et al. 1997. J. Biol. Chem. 272:9252–9259). These observations support a model for concerted roles of CaM isoforms in plant defense response against pathogens, in which the highly conserved CaM isoforms mediate ROS increases, while the divergent CaM isoforms activate programmed cell death and defense gene expression.

Transgenic plants constitutively expressing several other transgenes also have been shown to have lesion-mimic phenotype and altered disease resistance. These genes include Halobacterium opsin gene, mutant ubiquitin ubR48 gene, cholera toxin subunit Al gene, and yeast invertase (Beffa, R. et al. 1995. EMBO J. 14:5753–5761). These transgenic plants have elevated levels of endogenous SA, which argues that their altered disease resistance responses result from SA accumulation that may be ascribed to the metabolic stress induced by these transgenes (Durner, J. et al. 1997. Trends Plant Sci. 2:266–274). Therefore, it is not clear whether these genes are bona fide components of the plant defense response pathway(s). Thus, the divergent CaM isoforms represent one of the first "natural" pathogen-inducible components in plant defense signaling whose constitutive expression leads to enhanced disease resistance. The present invention not only enhance our understanding of the pathway(s) leading to plant disease resistance but also provide new opportunities to genetically engineer plants with resistant to a wide spectrum of pathogens.

EXAMPLES

The procedures in recombinant DNA technology described below are those well known and commonly employed in the art. These techniques and various other techniques are generally performed according to Sambrook et al., Molecular Cloning—A Laboratory Mannual, (1989). All general references are provided throughout this document. All informations contained herein are incorporated by reference.

EXAMPLE 1

Isolation of Calmodulin cDNAs from Soybean
Isolation of SCaM-4 cDNA clone from soybean A λZAP (Stratagene) soybean cDNA library, which was constructed from poly (A)+ RNA of half-apical and half-elongating regions of four day-old seedlings, was used for the isolation of SCaM cDNA clones. Library screening was performed by using ECL gene detection system (Amersham) according to the manufacturer's instruction. A rice genomic calmodulin clone, cam-2, was used as a probe DNA. Approximately 35,000 phages were plated on E.coli XL1-Blue and transferred to nylon membranes (Hybond N+, Amersham). The transferred membrane was denatured by soaking with 0.5 M NaOH, 1.5 M NaCl for 5 min. Then the membrane was neutralized by soaking twice with 0.5 M Tris-HCl (pH 8.0) and 1.5 M NaCl for 3 min period at room temperature. The membrane was alkaline-fixed by soaking with 0.4 N NaOH for 2 min. The membrane prehybridized with hybridization buffer containing 0.5 M NaCl and 5% blocking agent for 2 hr at 37° C. Then the membrane was hybridized with horseradish peroxidase-labelled probe DNA for 6 hr at 37° C. with gentle shaking. Posthybridization washes were performed twice in 6 M urea, 0.4×SSC, 0.5% SDS at 37° C. for 20 min followed by two washes in 2×SSC for 5 min at room temperate. Then the membrane was detected with detection reagent A, B for 1 min, and then exposed to X-OMAT AR film (Kodak) for 10 min. Positively hybridizing plaques were further purified with subsequent round of plaque hybridization.

To obtain cDNA insert, purified positive plaques were iii vivo excised to pBluescript-SK(−) with a helper phage R408. Two hundred microliters of XL1-Blue host cells ($O.D_{600}$=1.0) were mixed with 200 μl of λZAP phage stock containing about 1×10$^6$ pfu/ml, and 1 μl of R408 helper phage (1×10$^6$ pfu/ml). After incubation of the mixture at 37° C. for 15 min, 5 ml of 2×YT medium (Bacto tryptone 16 g, Bacto Yeast Extract 10 g and Sodium chloride 10 g each per 1 liter) were added. After incubation for 3 hr at 37° C. with shaking, the mixture was heated at 70 ° C. for 20 min to inactive the helper phage and to kill bacteria. The mixture was then centrifuged for 10 min at 4000 g and the supernatant was transferred to a sterile tube and stored at 4° C. To rescue excised phagemid from this stock, 200 μl of XL1-Blue host cells ($O.D_{600}$=1.0) and 200 μl of phage stock were combined, then incubated at 37° C. for 15 min. Then 50 μl of mixture was plated on LB/ampicillin plates followed by incubation at 37° C. for 12 hr. The ampicillin resistant colonies containing rescued phagemid were visible.

The sequencing reaction for double-stranded plasmid DNA was performed with Taq Dye Primer Cycling Sequencing Kit (Applied Biosystems) by using 373A automated DNA sequencer (Applied Biosystems Inc). Nucleotide sequence were analyzed using either DNASIS (Hitachi) on IBM PC or GCG package (Genetics Computer Group, Univ. of Wisconsin ) on DECstation 3300/Ultrix system.

A cDNA encoding soybean CaM was isolated by screening of the λ ZAP cDNA library with a rice genomic clone, cam-2, as a probe. From 62 positive clones out of 3.5×10$^4$ clones, SCaM-1, 2 and 3 were isolated and sequenced previously. Fifteen clones with very low intensity were randomly selected and screened 2 to 3 more times. Throughout the analysis of partial nucleotide sequencing and restriction enzyme mapping of these clones, one clone was selected which contain very long cDNA size and different restriction enzyme map pattern to compare with other SCaMs.

A finally selected clone was full-length cDNA and designated as SCaM4 (SEQ. ID No.:1). There are two HindIII and one EcoRI enzyme sites in internal sequence. Therefore, the HindIII fragment, two EcoRI—HindIII fragments were subcloned to pBluscript SK(−), and EcoRI-XhoI fragment was performed to self-ligation on pBluscript SK(−). Then, the fragments were sequenced by both orientation. The long HindIII fragment was sequenced by deletion sequencing method with ExoIII enzyme.
Isolation of SCaM-5 cDNA clone from soybean λ XZAP (Stratagene) soybean cDNA library, which was constructed from poly(A)+ RNA of the half-apical and half-elongating regions of four day-old seedlings, was used for the isolation of CaM cDNA clones. The library was screened by using ECL gene detection system (Amersham) according to the manufacturer's instruction. A rice genomic calmodulin clone, cam-2, was used as a probe DNA. Approximately 50,000 phages were plated on E.coli XL1-Blue and transferred onto nylon membranes (Hybond N+, Amersham). The transferred membrane was denaturated by soaking with 0.5 M NaOH, 1.5 M NaCl for 7 min. Then the membrane was neutralized by soaking with 0.5 M Tris-HCl (pH 7.5) and 1.5 M NaCl for 7 min at room temperature. The membrane was prehybridized with hybridization buffer containing 0.5 M NaCl and 5% blocking agent for 2 hr at 37°

C. The membrane was hybridized with a horseradish peroxidase-labelled probe DNA for 12 hr at 37° C. with gentle shaking. Post-hybridization washes were performed twice in 6 M urea, 0.4×SSC, 0.5% SDS at 37° C. for 20 min followed by two washes in 2×SSC for 5 min at 37° C. Positively hybridizing plaques were visualized by using the detection reagent A, B for I min, and exposed to X-OMAT AR film (Kodak) for 10 min. Positively hybridizing plaques were further purified by subsequent round of plaque hybridization.

To obtain cDNA inserts, purified positive plaques were in vivo excised to pBluescript-SK(−) with a helper phage R408 (Stratagene). Two hundred microliters of XL1-Blue host cells (O.D$_{600}$=1.0) were mixed with 200 µl of λ ZAP phage stock containing about 1×10$^6$ pfu/ml and 1 µl of helper phage R408. After incubation of the mixture at 37° C. for 15 min, 5 ml of 2×YT medium was added. After incubation for 3 hr at 37° C. with shaking, the mixture was heated at 70° C. for 20 min to inactivate the helper phages and to kill bacteria. The mixture was then centrifuged for 10 min at 400 g, and the supernatant was transferred to a sterile tube and stored at 4° C. To rescue excised phagemid from this stock, 200 µl of XL1-Blue host cells (O.D$_{600}$=1.0) and 100 µl of phage stock were combined, then incubated at 37° C. for 20 min. Then 50 µl of mixture was plated on LB/ampicillin plates followed by incubation at 37° C. for 15 hr. The ampicillin resistant colonies were examined for the presence of appropriate phagemids by alkaline lysis minipreps.

The sequencing reaction for double-stranded plasmid DNA was performed with a Taq Dye Primer Cycling sequencing Kit (Applied Biosystems) by using 373A automated DNA sequencer (Applied Biosystems Inc) as specified by the manufacturer. Nucleotide sequences were analyzed using either a DNASIS (Hitachi Engineering Co.) on IBM PC or GCG package (Genetics Computer Group, Univ. of Wisconsin ) on DECstation 3300/Ultrix system (Digital Equipment Corporation).

A cDNA encoding soybean CaM was isolated by screening of λ ZAP cDNA library with a rice genomic clone, cam-2, as a probe. From 62 positive clones out of 3.5×10$^4$ clones, SCAM-1, -2, -3 and -4 were isolated and sequenced previously. But the fifth clone was truncated in 5' region. To obtain a full-length clone, the library was re-screened with a specific probe made from the 3' untranslated region. Throughout the analysis of partial nucleotide sequencing and restriction enzyme mapping of four clones, one clone was selected which has the same nucleotide sequence to the truncated clone. A selected clone was shown to be a full-length cDNA. This clone was designated as a SCaM-5. There are one EcoRI and one SacI enzyme sites in internal sequence.

EXAMPLE 2

Construction of Expression Vectors
Construction of plasmid pLES9804
For the overexpression of SCaM-4 (SEQ. ID No.:1) in tobacco plant, binary vectors were constructed that contained SCaM-4 under the control of the cauliflower mosaic virus 35S subunit (CaMV35S) promoter region and the Agrobacterium nopaline synthase terminator. pGA643 binary vector (An, G. et al. 1988. In Plan Molecular Biology Mannual, eds. Gelvin, S. B. & Schilperoort, R. A., Kluwer Academic, Dordrecht, A3) was digested with HpaI. SCAM-4 cDNA was digested with RsaI. The RsaI-digested 854bp DNA fragment from SCaM-4 cDNA is directly cloned into the HpaI-digested pGA643 vector to give pLES9804. Said vector in Agrobacterium tumefaciens EHA101/pLES9804 has been deposited to Korean Collection for Type Culture Korean Research Institute of Bioscience and Biotechnology (KRIBB) #52, Oun-dong, Yusong-ku, Taejon 305–333, Republic of Korea, on Nov. 10, 1998 according to Budapest Treaty (KCTC Accession No. 0545BP).
Construction of plasmid pLES9805
For the overexpression of SCaM-5 (SEQ. ID NO.:3) in tobacco plant, binary vectors were constructed that contained SCaM-5 under the control of the cauliflower mosaic virus 35S subunit (CaMV35S) promoter resion and the Agrobacterium nopaline synthase terminator. pGA643 binary vector was digested with HpaI. SCaM-5 cDNA was digested with EcoRI. Both ends of the DNA fragment (562bp) from SCaM-5 cDNA was converted to blunt ends with an appropriate of Klenow fragment and, by ligation with T4 DNA ligase, cloned into the binary vector to give pLES9805. Said vector in Agrobacterium tumefaciens EHA101/pLES9805 has been deposited to Korean Collection for Type Culture Korean Research Institute of Bioscience and Biotechnology (KRIBB) #52, Oun-dong, Yusong-ku, Taejon 305–333, Republic of Korea, on Nov. 10, 1998 according to Budapest Treaty (KCTC Accession No. 0546BP).

EXAMPLE 3

Generation of Transgenic Tobacco Plants.

The transgenic tobacco plants expressing SCaM4 were generated by Agrobacterium-medeated leaf disc transformation (Horsch, R. B. et al. 1988. In Plant Molecular Biology Mannual, eds. Gelvin, S. B. & Schilperoort, R. A., Kluwer Academic, Dordrecht, A5). Tobacco leaf discs were prepared from 8-week-old young tobacco plant and soaked in a solution containing MS salts, 3% sucrose, 2 mg/l NAA, 0.5 mg/l BA, and 0.05% MES for 5 min. The leaf discs were inoculated with Agrobactrium tumefaciens EHA101 harboring the construct pLES9804 for 2 days. After washing with sterile MS basal medium the leaf discs were transferred onto selection medium (0.5 mg/l BA, MS salts, 3% sucrose, 100 mg/l kanamycin, 250 mg/l sudopen, and 0.8% agar). After 1 month, regenerated shoots were transferred onto the rooting media containing MS salts, 3% sucrose, 100 mg/l kanamycin, 250 mg/l sudopen and 0.8% agar. Rooted plants were transferred to a mixed bed of vermiculite, perlite, and peat moss(1:1:1) and grown at 25° C. with an 16 hrs day-length cycle in a growth chamber. Thirty two regenerated plants were grown. Among them 13 plants expressed SCaM4 transcripts and SCaM4 protein.

The transgenic tobacco plants expressing SCaM-5 were generated by Agrobacterium-medeated leaf disc transformation. Tobacco leaf discs were prepared from 8-week-old young tobacco plant and soaked in a solution containing MS salts, 3% sucrose, 2 mg/l NAA, 0.5 mg/l BA, and 0.05% MES for 5 min. The leaf discs were inoculated with Agrobactrium tumefaciens harboring the construct pLES9805 for 2 days. After washing with sterile MS basal medium the leaf discs were transferred onto selection medium( 0.5 mg/l BA, MS salts, 3% sucrose, 100 mg/l kanamycin, 250 mg/l sudopen, and 0.8% agar). After I month, regenerated shoots were transferred onto the rooting media containing MS salts, 3% sucrose, 100 mg/l kanamycin, 250 mg/l sudopen and 0.8% agar. Rooted plants were transferred to a mixed bed of vermiculite, perlite, and peat moss(l:1:1) and grown at 25° C. with an 16 hrs day-length cycle in a growth chamber. Twenty seven regenerated plants were grown on the soil. Among them 19 independent transgenic plant lines expressed SCaM-5 transcripts and proteins.

$R_1$ progeny of transgenic plants expressing high level of SCaM4 or SCaM5 was used for the experiments and maintained at 25° C. day and 20° C. night temperature, a 16-h photoperiod, and 65% relative humidity.

EXAMPLE 4

Analysis of SCaM expression in Transgenic Plants

Immnoblotting-Polyclonal antibodies against two SCaM isoforms, SCaM-1 and SCaM4, were prepared by immunizing goats subcutanepusly with 10 mg of each purified SCaM protein in the Freund's complete adjuvant. Subsequent boosting injection were done at 3-week intervals with 1 mg of protein in the Freund's incomplete adjuvant. Fifty micrograms of isolated total soluble protein from wild-type and independent transgenic plant lines were electrophoresed on 13.5% SDS polyacrylamide gels. Proteins were transferred onto a PVDF membrane (Millipore) and incubated with either anti-SCaM-1 or anti-SCaM4 antibody. Protein bands were detected using the ECL system after incubating with horseradish peroxidase-conjugated antigoat IgG (ICN Biomedicals). The amounts of SCM-4 or SCaM5 protein in the transgenic tobacco plants were estimated to be 0.3 or 0.5 µg per mg total soluble leaf protein, respectively.

Northern blot hybridization-Total RNA was isolated from a wild-type, a control transgenic plant harboring an empty vector, and three representative independent transgenic plants expressing SCaM-4 or SCaM5. Ten µg of isolated total RNA was separated on denaturing 1.5% agarose formaldehyde gels. Ethidium bromide was included to verify equal loading of RNA. After transfer to Gene Screen membranes, filter were hybridized with $^{32}$P-labelled gene-specific probe in Church's buffer at 65° C. for 16 hrs. SCaM4 specific probe was cut out from SCaM4 or SCaM-5 cDNA with EcoRI and XhoI and was gel purified. After incubating, filters were washed for 20 min with 2×SSC twice, for 20 min with 1×SSC twice, for 20 min with 0.5×SSC once, and then for 20 min with 0.5×SSC, 0.1% SDS at 60° C. once. Filters were exposed to X-ray films at −80° C. for 1 hr to 6 days.

EXAMPLE 5

Analysis of the Disease Resistance of Transgenic Plants

Figure 6:
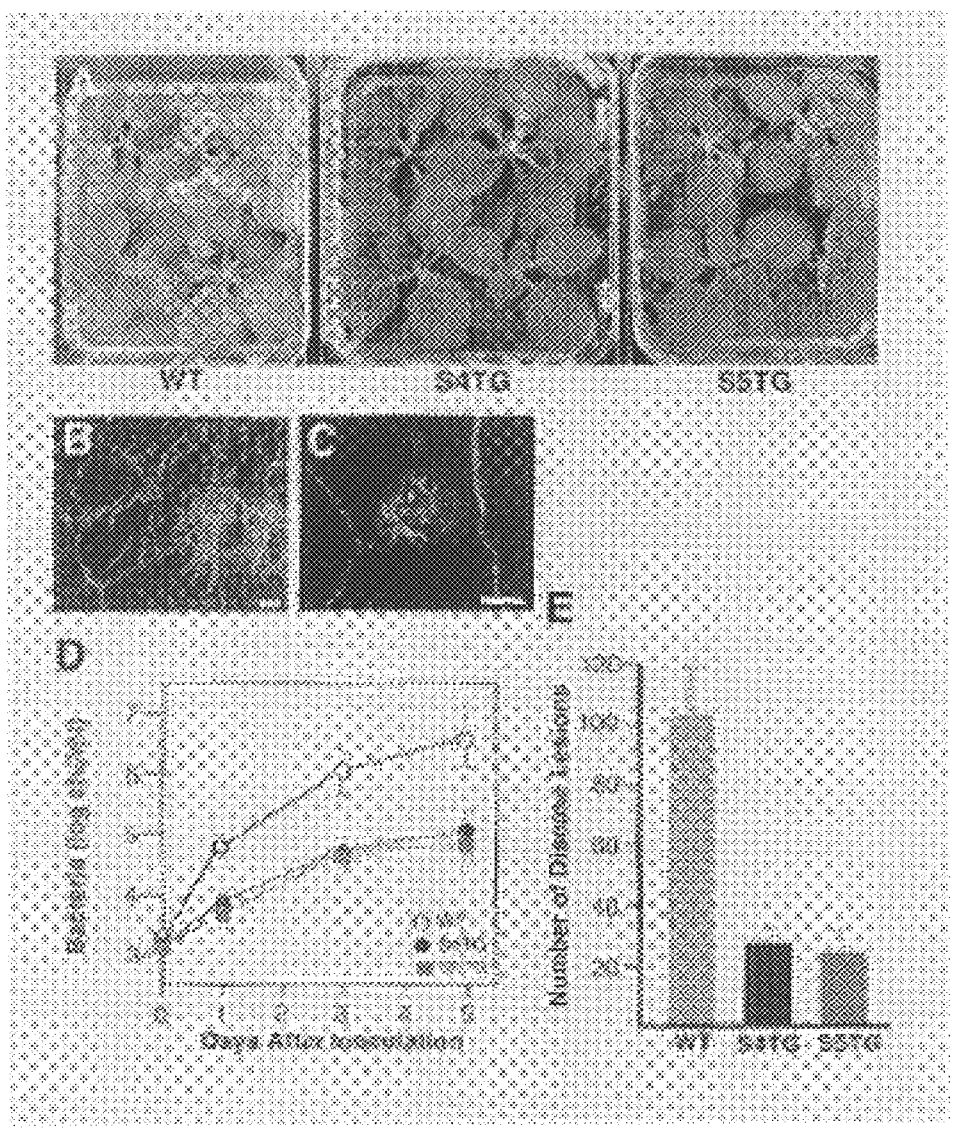

The invention transgenic tobacco plants, described above, were subjected to the fungal, bacterial and viral infection assays. The results are shown in FIG. 6. TMV treatment—Tobacco plants [*Nicotiana tabacum* cv. Xanthi nc (NN)/SCaM-4 or -5 transgenic] were grown at 25° C. in a growth chamber programmed for a 16-hr light cycle. Seven- to eight-week-old tobacco plants were either inoculated by rubbing fully expanded leaves with carborundum plus TMV (U1 strain, 2 µg/ml or as indicated in 50 mM phosphate buffer, pH 7.0) or buffer only (mock). After infection, plants were washed by spraying sterile water to remove the carborundum from the leaves. The plants were maintained at 25° C. throughout the infection in a growth chamber. The development of HR lesions were monitored over 5 days. An empty vector transgenic plants were simultaneously tested as a control.
Fungus treatment—*Phytophthora parasitica* pv. *nicotianae* mycelia were suspended in sterile water and spread-plated on V8 agar plates [200 ml of V8 juice, 3.0 g of $CaCO_3$, and 18 g of agar per liter (pH 6.15)] supplemented with I g of dried tobacco leaves per liter and incubated at 25° C. in a continuous light. After a mycelial lawn was established (2–4 weeks), small squares (~8 mm$^2$) were cut and adhered on the agar media (under 4-week-old tobacco plants). They were transferred to an incubation chamber at 25° C. with a 16-hr photopered. The development of HR lesions were monitored over 5 days. An empty vector transgenic plants were simultaneously tested as a control.

Bacteria treatment—*Pseudomonas syringae* pv. *tobaci* (ATCC 11528) were grown at 28° C. overnight in King's B medium containing 50 µg/ml rifampicin, washed twice, resuspended, and diluted in 10 mM $MgCl_2$. Small areas of healthy leaves were inoculated by infiltration with a suspension of 10$^5$ bacterial cells per ml using a 1 -ml hypodermic syringe without a needle. One side of each leaf was inoculated as four different places with ~20 µl of bacterial suspension per wound, and the other side was mock-inoculated with 20 µl of 10 mM $MgCl_2$. Leaf discs (6mm diameter) was collected with a puncher. Bacteria were extracted by maceration of leaf discs in 10 mM $MgCl_2$ and serial dilutions were plated on King's B media with 50 µg per ml rifampicin and 10 µg per ml malidixic acid. Colonies were counted at 48 hrs after incubation at 28° C. In planta bacterial growth was monitored over 5 days. The development of HR lesions were monitored over 5 days. An empty vector transgenic plants were simultaneously tested as a control.

The transgenic tobacco plants, which were transformed with pLES9804 or pLES9805, respectively, and ultimately revealed a multiple disease resistance to a wide variety of pathogens, have been deposited to Korean Collection for Type Cultures according to the Budapest Treaty (KCTC Accession No. 0543BP and 0544BP, respectively).

TABLE 1

Endogenous salicylic acid (SA) levels in transgenic SCaM-4 and SCaM-5 plants.

| | Uninfected | TMV-infected | |
|---|---|---|---|
| Plants | Free SA | Free SA | Bound SA |
| Wild type | 0.042 ± 0.005 | 2.8 ± 0.5 | 2.2 ± 0.5 |
| Transgenic SCaM-4 | 0.031 ± 0.010 | 4.1 ± 1.0 | 2.4 ± 0.8 |
| Transgenic SCaM-5 | 0.035 ± 0.005 | 2.5 + 0.5 | 1.6 ± 0.5 |

The levels of SA (µg/g fresh weight) were determined from the top forth or fifth middle leaves of mature plants as described (Herbers, K. et al. 1996. Plant Cell 8:793–803). Data are the means of two determinations from five independent transgenic plant lines. Bound SA levels were below detection-limit in uninfected plants. Endogenous SA levels from tobacco mosaic virus (TMV)-infected plants were determined 10 days after inoculation.

What is claimed is:

1. A binary vector comprising a nucleotide sequence encoding ScaM5 protein (SEQ ID NO:4) and regulatory elements for the expression of ScaM5 in plant cells wherein the regulatory elements comprise a promoter and a transcription termination sequence.

2. The binary vector according to claim 1 wherein said regulatory elements are the 35S promoter from cauliflower mosaic virus, a translation enhancer sequence, and the nopaline synthase transcription termination sequence.

3. The new binary vector of claim 1 wherein the promoter is a constitutive promoter.

4. The binary vector of claim 1 wherein the promoter is an inducible promoter.

5. The binary vector of claim 1 wherein promoter is the 35S promoter from cauliflower mosaic virus.

6. The binary vector of claim 1 further comprising a translation enhancer sequence.

7. The binary vector pLES9805.

8. A transgenic plant cell which is transformed with and expresses a gene encoding soybean calmodulin 5 (Scam5) protein (SEQ ID NO:4), or the transgenic progeny of said plant cell.

9. The transgenic plant cell of claim 8 which is a dicot.

10. The plant cell according to claim 8 wherein the gene encoding the soybean calmodulin 5 protein is SEQ ID NO:3.

11. The transgenic plant cell of claim 9 which is tobacco.

12. A transgenic plant, the cells of which express the gene contained in the vector pLES9805 (KCTC Accession No. 0546BP) encoding ScaM5 or the transgenic progeny of said plant.

13. The transgenic plant of claim 12 wherein the plant is a dicot.

14. The transgenic plant of claim 13 wherein the plant is tobacco.

15. A multiple disease resistant transgenic plant which contains in its genome a structural gene comprising in operable linkage:
   (i) a promoter functional in plant cells to cause the production of an RNA sequence,
   (ii) a nucleic acid sequence encoding a soybean calmodulin 5 (SEQ ID NO:4) protein; and
   (iii) a 3' non-translated region which functions in plant cells to cause the termination of transcription and the addition of polyadenylated ribonucleotides to the 3' end of transcribed mRNA sequences.

16. The multiple disease resistant transgenic plant of claim 15 which is a dicot species.

17. A method for enhancing multiple disease resistance of a higher plant to attack by one or more plant pathogens by transforming said plant with a gene encoding ScaM5(SEQ ID NO:4) to produce a transformed plant, wherein said transformed plant has enhanced multiple disease resistance as compared to an untransformed plant.

18. The method of claim 17 wherein the plant is a dicot.

19. The method of claim 17 wherein the gene is contained in a binary ScaM5 gene vector.

20. The method of claim 19 wherein the binary ScaM5 gene vector further comprises regulatory elements for the expression of ScaM5 in plant cells.

21. The method of claim 19 wherein the binary ScaM5 gene vector is pLES9805 (KCTC Accession No. 0546BP).

22. A method for enhancing multiple disease resistance of a plant wherein said plant is susceptible to plant pathogens comprising the steps of:
   (a) transforming plant cells with a chimeric recombinant DNA molecule comprising in operable linkage:
      (i) a promoter functional in plant cells to cause the production of an RNA sequence;
      (ii) a structural gene encoding a soybean calmodulin 5 (SEQ ID NO:4) protein; and
      (iii) a 3' non-translated region which functions in plant cells to cause the termination of transcription and the addition of polyadenylated ribonucleotides to the 3' end of transcribed MRNA sequences; and
   (b) regenerating said plant cells to provide a differentiated plant, wherein said differentiated plant has enhanced multiple disease resistance as compared to an untransformed plant.

23. The method of claim 22 wherein said plant is a dicot species.

24. The method of claim 22 wherein said plant is tobacco.

25. The method of claim 22 wherein the structural gene has the nucleotide sequence of SEQ ID NO:3.

26. The method of claim 22 wherein the chimeric recombinant DNA molecule is contained in a binary vector.

* * * * *

SEQUENCE LISTING

<160> NUMBER OF SEQ ID NOS: 4

<210> SEQ ID NO 1
<211> LENGTH: 1401
<212> TYPE: DNA
<213> ORGANISM: G. max calmodulin4 (SCaM4)
<220> FEATURE:
<221> NAME/KEY: CDS -continued

<222> LOCATION: (657)..(1106)

<400> SEQUENCE: 1

| | |
|---|---|
| atttcttacc tctgtaggaa aaatcaaact cacatactta ccggatgagt ctgtttctta | 60 |
| ccgaggacaa gctttataag tgtctgagtc agtcttctgg tgcaagcaaa gcaaccagct | 120 |
| agcgtggtct ttgggtgggt ggtgtgtgga aattggatat tgatgagaac gcagactcta | 180 |
| cacacctccc catactccat actccatacc cttttcaagt ttgaattaat cccttcttgt | 240 |
| tttgtcccct aaacaccaaa cccttccagc tgtcaagatt ttctccgtat tatactaatc | 300 |
| aaattaaata tcatcataca ttaaaaaatc attcagcgca tttaaaccat cgtgccccac | 360 |
| cccatttgta ctatactact atgtaacaat tacaattaca atgtgattct tttttacaca | 420 |
| ataaagccac gagtatggca acaaaatgca agtcatatac ttaatttgac tcggtaaatt | 480 |
| aaaattttaa aagaaatctt gcaagactag ctagctagca tcacctaagt tctacaatat | 540 |
| agcccagcta ggattgagct atactcaact caacacatca ttctctcttt ccctctctat | 600 |
| ctctatctct ctttctctgt ctcttttctg gttgaagttt gaaagacaaa tacacc | 656 |

| | | |
|---|---|---|
| atg gca gat atc ctg agt gaa gaa cag att gtt gat ttt aaa gag gcc | | 704 |
| Met Ala Asp Ile Leu Ser Glu Glu Gln Ile Val Asp Phe Lys Glu Ala | | |
| 1               5                   10                  15 | | |
| ttt ggc ttg ttt gac aaa gat gga gat ggt tgc att act gtg gaa gaa | | 752 |
| Phe Gly Leu Phe Asp Lys Asp Gly Asp Gly Cys Ile Thr Val Glu Glu | | |
|         20                  25                  30 | | |
| ctt gcc act gtc att cgg tca ttg gat cag aac ccc act gaa gaa gag | | 800 |
| Leu Ala Thr Val Ile Arg Ser Leu Asp Gln Asn Pro Thr Glu Glu Glu | | |
| 35                  40                  45 | | |
| ctc caa gat atg ata agc gaa gtc gat gca gat ggc aat gga acc att | | 848 |
| Leu Gln Asp Met Ile Ser Glu Val Asp Ala Asp Gly Asn Gly Thr Ile | | |
| 50                  55                  60 | | |
| gaa ttt gac gag ttc ttg agc ttg atg gcc aag aaa gtt aaa gac act | | 896 |
| Glu Phe Asp Glu Phe Leu Ser Leu Met Ala Lys Lys Val Lys Asp Thr | | |
| 65                  70                  75                  80 | | |
| gat gca gag gag gag ctc aaa gaa gct ttc aag gtt ttt gac aaa gat | | 944 |
| Asp Ala Glu Glu Glu Leu Lys Glu Ala Phe Lys Val Phe Asp Lys Asp | | |
|                 85                  90                  95 | | |
| caa aat ggc tac ata tca gct agt gag ttg aga cac gta atg atc aat | | 992 |
| Gln Asn Gly Tyr Ile Ser Ala Ser Glu Leu Arg His Val Met Ile Asn | | |
|             100                 105                 110 | | |
| cta ggg gaa aaa cta acc gat gaa gag gtg gag cag atg att aaa gaa | | 1040 |
| Leu Gly Glu Lys Leu Thr Asp Glu Glu Val Glu Gln Met Ile Lys Glu | | |
|         115                 120                 125 | | |
| gca gat ttg gac ggt gat ggc caa gtt aac tat gag gaa ttc gtc aag | | 1088 |
| Ala Asp Leu Asp Gly Asp Gly Gln Val Asn Tyr Glu Glu Phe Val Lys | | |
| 130                 135                 140 | | |
| atg atg atg acc gtt cga tgaa acactctcac ctaattaatt ggattggaca | | 1140 |
| Met Met Met Thr Val Arg | | |
| 145                 150 | | |

| | |
|---|---|
| ccaatttgtt aattcaaaat tcattggctt ccaacctccc aatgaaataa gtgttctttc | 1200 |
| tttattattg tttgttgtat tgtactatta ttctacttgt acttagtaat gaccaagcag | 1260 |
| tagattggca cccccattcc atttgatcca ttccaaaatt aaattactat tcttgtaatt | 1320 |
| ttagttcagt acattttcta tcctccgaga gtaagaaacc caaggagcat atctacccat | 1380 |
| taattatgca tgacttttac c | 1401 |

<210> SEQ ID NO 2
<211> LENGTH: 150

-continued

```
<212> TYPE: PRT
<213> ORGANISM: G. max calmodulin4 (SCaM4)

<400> SEQUENCE: 2

Met Ala Asp Ile Leu Ser Glu Glu Gln Ile Val Asp Phe Lys Glu Ala
 1               5                  10                  15

Phe Gly Leu Phe Asp Lys Asp Gly Asp Gly Cys Ile Thr Val Glu Glu
            20                  25                  30

Leu Ala Thr Val Ile Arg Ser Leu Asp Gln Asn Pro Thr Glu Glu Glu
        35                  40                  45

Leu Gln Asp Met Ile Ser Glu Val Asp Ala Asp Gly Asn Gly Thr Ile
    50                  55                  60

Glu Phe Asp Glu Phe Leu Ser Leu Met Ala Lys Lys Val Lys Asp Thr
 65                 70                  75                  80

Asp Ala Glu Glu Glu Leu Lys Glu Ala Phe Lys Val Phe Asp Lys Asp
                85                  90                  95

Gln Asn Gly Tyr Ile Ser Ala Ser Glu Leu Arg His Val Met Ile Asn
            100                 105                 110

Leu Gly Glu Lys Leu Thr Asp Glu Glu Val Glu Gln Met Ile Lys Glu
        115                 120                 125

Ala Asp Leu Asp Gly Asp Gly Gln Val Asn Tyr Glu Glu Phe Val Lys
    130                 135                 140

Met Met Met Thr Val Arg
145                 150

<210> SEQ ID NO 3
<211> LENGTH: 916
<212> TYPE: DNA
<213> ORGANISM: G. max calmodulin5 (SCaM5)
<220> FEATURE:
<221> NAME/KEY: CDS
<222> LOCATION: (69)..(518)

<400> SEQUENCE: 3
ctccctctct cttttctaag tcacaaaata ttgtcttagt tttcatttga agctcaaaca        60 ttaacacc  atg gca gat gtt ctg agt gaa gaa cag att agt gag atc aaa      110
          Met Ala Asp Val Leu Ser Glu Glu Gln Ile Ser Glu Ile Lys
           1               5                  10 gaa gcc ttt ggc ttg ttt gac aaa gat ggt gat ggg tgc att act gtg      158
Glu Ala Phe Gly Leu Phe Asp Lys Asp Gly Asp Gly Cys Ile Thr Val
 15                  20                  25                  30 gac gaa ttt gtc acg gtt atc cgg tca ttg gtt cag aac ccc aca gaa      206
Asp Glu Phe Val Thr Val Ile Arg Ser Leu Val Gln Asn Pro Thr Glu
                 35                  40                  45 gaa gag ctc caa gac atg ata aac gag gta gat gca gat ggt aat gga      254
Glu Glu Leu Gln Asp Met Ile Asn Glu Val Asp Ala Asp Gly Asn Gly
         50                  55                  60 acc att gaa ttt gtt gag ttt ttg aac tta atg gcc aag aaa atg aag      302
Thr Ile Glu Phe Val Glu Phe Leu Asn Leu Met Ala Lys Lys Met Lys
 65                  70                  75 gaa act gat gaa gag gaa gat ctc aaa gag gct ttc aag gtg ttt gac      350
Glu Thr Asp Glu Glu Glu Asp Leu Lys Glu Ala Phe Lys Val Phe Asp
 80                  85                  90 aag gat caa aat ggc tac att tca gca agt gag ttg aga cac gtt atg      398
Lys Asp Gln Asn Gly Tyr Ile Ser Ala Ser Glu Leu Arg His Val Met
 95                  100                 105                 110 atc aat ctg ggt gaa aaa cta act gat gag gag gtg gag cag atg att      446
Ile Asn Leu Gly Glu Lys Leu Thr Asp Glu Glu Val Glu Gln Met Ile
             115                 120                 125
```

```
gaa gaa gca gat ttg gat ggt gat ggt caa gtt aat tat gat gaa ttt      494
Glu Glu Ala Asp Leu Asp Gly Asp Gly Gln Val Asn Tyr Asp Glu Phe
            130                 135                 140 gtc aag atg atg atg act att gga          tg aaattttcaa acaacaaatt     540
Val Lys Met Met Met Thr Ile Gly
        145                 150 tattgttcga attcgatcat ttgggcccca atctcattca ctcgcatgaa ataataagtc     600
ttccaatcaa tttttggtgt attttacttg tagcacatga tatgaatgac caatgtatta     660
gagtgacatc tcagccaatt tgatttgttc aaactccaac ccataattat tctttcagtt     720
ttagtttagc attccttatg ttttaaaatt aattagaggg aatttattca agaacttctg     780
aaattagact cttttttgaa agattaatgt atgctacaat ttattctttc tcttgtgaac     840
atggtattgc tacaatttat ttatatcatt cagaaaaata aaaacagca caagaattaa      900 acaaaaaaaa aaaaaa                                                      916
```

<210> SEQ ID NO 4
<211> LENGTH: 150
<212> TYPE: PRT
<213> ORGANISM: G. max calmodulin5 (SCaM5)

<400> SEQUENCE: 4

```
Met Ala Asp Val Leu Ser Glu Glu Gln Ile Ser Glu Ile Lys Glu Ala
 1               5                  10                  15

Phe Gly Leu Phe Asp Lys Asp Gly Asp Gly Cys Ile Thr Val Asp Glu
             20                  25                  30

Phe Val Thr Val Ile Arg Ser Leu Val Gln Asn Pro Thr Glu Glu Glu
         35                  40                  45

Leu Gln Asp Met Ile Asn Glu Val Asp Ala Asp Gly Asn Gly Thr Ile
     50                  55                  60

Glu Phe Val Glu Phe Leu Asn Leu Met Ala Lys Lys Met Lys Glu Thr
 65                  70                  75                  80

Asp Glu Glu Glu Asp Leu Lys Gly Ala Phe Lys Val Phe Asp Lys Asp
                 85                  90                  95

Gln Asn Gly Tyr Ile Ser Ala Ser Glu Leu Arg His Val Met Ile Asn
                100                 105                 110

Leu Gly Glu Lys Leu Thr Asp Glu Glu Val Glu Gln Met Ile Glu Glu
            115                 120                 125

Ala Asp Leu Asp Gly Asp Gly Gln Val Asn Tyr Asp Glu Phe Val Lys
        130                 135                 140

Met Met Met Thr Ile Gly
145                 150
```